(12) United States Patent
Bosworth et al.

(10) Patent No.: US 8,738,550 B2
(45) Date of Patent: *May 27, 2014

(54) RISK FACTOR ENGINE THAT DETERMINES A USER HEALTH SCORE

(71) Applicant: Keas, Inc., San Francisco, CA (US)

(72) Inventors: Adam Bosworth, San Francisco, CA (US); George Kassabgi, Winchester, MA (US); Stephan Richter, Maynard, MA (US); Stu Statman, San Francisco, CA (US)

(73) Assignee: Keas, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/015,354

(22) Filed: Aug. 30, 2013

(65) Prior Publication Data

US 2013/0346355 A1    Dec. 26, 2013

Related U.S. Application Data

(63) Continuation of application No. 12/623,992, filed on Nov. 23, 2009, now Pat. No. 8,560,479.

(51) Int. Cl.
*G06F 15/18*   (2006.01)

(52) U.S. Cl.
USPC .......................................................... 706/12

(58) Field of Classification Search
USPC .............................. 706/12, 45, 62
See application file for complete search history.

(56) References Cited

U.S. PATENT DOCUMENTS

| | | | |
|---|---|---|---|
| 6,269,339 B1 | 7/2001 | Silver | |
| 7,577,475 B2 | 8/2009 | Cosentino | |
| 7,730,063 B2 | 6/2010 | Eder | |
| 8,560,479 B2 | 10/2013 | Bosworth | |
| 2005/0113650 A1 | 5/2005 | Pacione | |
| 2007/0072156 A1 | 3/2007 | Kaufman | |
| 2007/0244375 A1 | 10/2007 | Jenkins | |
| 2008/0133272 A1 | 6/2008 | Marshall | |
| 2008/0195594 A1 | 8/2008 | Gerjets | |
| 2008/0319796 A1* | 12/2008 | Stivoric et al. ................... 705/3 |
| 2008/0319855 A1* | 12/2008 | Stivoric et al. ................. 705/14 |
| 2011/0045619 A1 | 2/2011 | Ling | |

OTHER PUBLICATIONS

Zahariadis, Evolution of the Wireless PAN and LAN standards, 2004, Elsevier, pp. 1-11.
U.S. Appl. No. 12/623,992 Final Office Action mailed Feb. 7, 2013.
U.S. Appl. No. 12/623,992 Office Action mailed Aug. 14, 2012.

* cited by examiner

*Primary Examiner* — David Vincent
(74) *Attorney, Agent, or Firm* — Lewis Roca Rothgerber LLP

(57) ABSTRACT

A method for processing risk factors for a user is disclosed. The method may include receiving protocol data for creating a risk factor engine by an application stored and executed at a computing device. The risk factor engine may be stored in memory and executable by a processor to process a first set of stored user health data for a user. The protocol data may include a rule and one or more health attribute values. The rule and the one or more health attribute values may each include a computer programming expression editable by an administrator. The method may further include determining a user health score through execution of the risk factor engine by the processor and based on the user health data.

18 Claims, 7 Drawing Sheets

FIG. 3 keas

| My Coaches | All Coaches |

Labs_Low_density
Lipoprotein_Last
Modified: *12/3/08*
Created By: *unknown*

Details
Ranges
Goals
Calculated Attributes
Functions
Rules
Test Plan
Tools and Settings

COACHES | QUESTIONNAIRES | ATTRIBUTES | ADMIN

Keas Manager    Log Out

⬚✕⬚⬇⬚⬆

Name LOL_Healthy_Greater than 190  ⓘ
Description Healthy, non-smoker, LOL >190  ⓘ
If condition ⬇ not calc.HeartDisease and not calc.PreventHeart  ⓘ
    Disease and not calc.Diabetes and LDL >= 190
Take action notify ▼
            Reason
            Plan Recent LDL value
            Tag LOL_Healthy_Greater than 190
            Select tag or enter one
            select one▼
            Message
            Required ○yes ⦿no
            confirmation
            Every no value ▼
            Else action Select action ▼
Quick Test no value ▼
[Test]

[Cancel] [Save]

RISK FACTOR ENGINE THAT DETERMINES A USER HEALTH SCORE

CROSS-REFERENCE TO RELATED APPLICATION

This application is a continuation of U.S. patent application Ser. No. 12/623,992, filed Nov. 23, 2009 and entitled "Risk factor coaching engine that receives protocol data including a rule and a health attribute value, and determines a user health score," the disclosure of which is hereby incorporated by reference.

BACKGROUND OF THE INVENTION

1. Field of the Invention

The present invention generally relates to user health assessment. The present invention more specifically relates to determining the effects of risk factors on user health.

2. Description of the Related Art

Keeping track of various aspects of personal health is an important part of living a long and productive life. To that end, various services are available to assist people in tracking different aspects of their health. For example, numerous web services provide general health information to a user. These informational services provide articles, discussion forums, and other educational information. These web services allow users to search, retrieve, and review content of particular interest or applicability. For example, one existing web service provides specific information for diabetes while another service provides information related to controlling blood pressure.

Other web services provide calorie information for foods that a user might eat. Such services allow users to list those foods consumed by the user and calculate a corresponding breakdown of the calories. This type of service is inconvenient, however, in that it requires a user to track all foods that are eaten throughout the course of a day much less a single meal. Most users, too, do not take the initiative to provide their meal information to the meal tracking service to access calorie information. These meal tracking services typically return the number of calories consumed and little additional information. The usefulness of such services is thereby reduced.

Some web services allow a user to submit a question to a practitioner with experience related to the subject matter of the question. The web service will then "post" or otherwise publish the answer to the user's question after some period of time. These web services do not consider any personal information about the user when addressing their question and may provide only broad-based and generalized information that is unlikely to be individually tailored to the requesting user. Further, the answer is posted by the web service and is not kept confidential between the user and the practitioner.

There is a need in the art for a health service that provides health information specific to the needs and health risks of a particular user. Such a service should offer ease of use not only for the end user but also for the entity providing the health information tailored for the particular user.

SUMMARY OF THE CLAIMED INVENTION

A method for processing risk factors may include receiving protocol data for creating a risk factor engine by an application stored and executed at a computing device. The risk factor engine may be stored in memory and executable by a processor to process a first set of stored user health data for a user. The protocol data may include a rule and one or more health attribute values. The rule and the one or more health attribute values may each include a computer programming expression editable by an administrator. The method may further include determining a user health score through execution of the risk factor engine by the processor and based on the user health data. Determining the user health score may include evaluating the expressions of the one or more health attribute values by inputting the user health data to calculate one or more calculated health attribute values, and then evaluating the expression of the rule by inputting the one or more calculated health attribute values to calculate the user health score.

Embodiments of the method can be performed by a computing device in communication with a client or by the client itself. The method can also be performed by a processor executing a program contained on a computer readable non-transitory storage medium.

BRIEF DESCRIPTION OF THE DRAWINGS

FIG. 3 illustrates an interface for setting calculated attributes for a risk factor.

FIG. 4 illustrates an interface for setting a rule for execution on risk factor data.

FIG. 5 illustrates an interface for providing a user health prediction to a user.

FIG. 6 illustrates an alternative implementation of an interface for providing user health predictions to a user.

DETAILED DESCRIPTION

Risk factor data can be processed by a risk factor coaching engine to determine health risks for a user. Embodiments of the present invention allow for identification of user health risks and performing actions based on user health data associated with those risks. A risk factor coaching engine executed within a health coaching protocol may be configured for identifying and processing user data. The risk factor coaching engine may perform actions to provide a user that is subject to health risks with information, recommendations, alerts via other coaching engines, and appointments with health care professionals. The risk factor coaching engine may also predict attribute values for a user based on a time period and goals for user health data upon which the predicted attribute value is based.

The presently disclosed protocol authoring system and coaching engines are flexible in that they consider information from a variety of sources to determine risks to the health of a user. The protocol may incorporate physical, social, family, and other health related data of the user. The protocol may process both singularly occurring actions as well as those that occur repeatedly over time and that may be based on observed trends. Feedback regarding user health risks may be provided to a user based on the most recent user data as well as progress-good or bad-made by the user.

Figure 1:
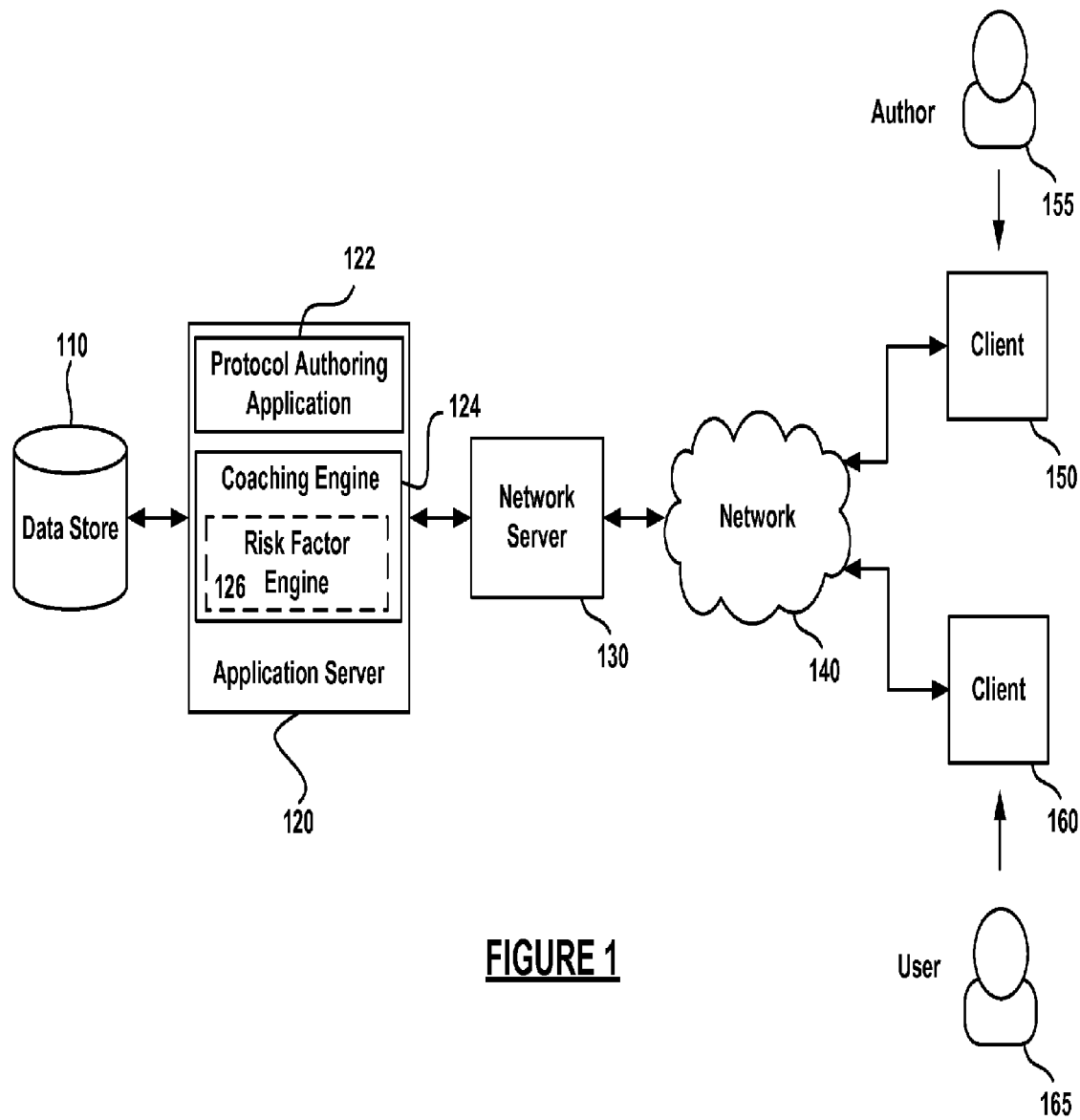
FIG. 1 is an exemplary system for authoring a protocol for identifying and processing user health risk data.

FIG. 1 is an exemplary system for authoring a protocol for identifying and processing user health risk data. The system of FIG. 1 includes data store 110, application server 120, and network server 130. Data store 110 stores user health data including attribute, range, protocol, goal, and other data. Data store 110 can be implemented as a logical data store on the same computing device as coaching engine 124, as one or more separate machines accessible by coaching engine 124, or a combination of the foregoing. The user health data can include health risk data for a user such as user age, weight, diabetes diagnosis, diabetes type, birthday, gender, height, coronary heart disease diagnosis, hemoglobin data, HDL, LDL, blood pressure, medications, stress level, sleep habit information, nutrition information, alcohol consumption and smoking habits.

Figure 3:
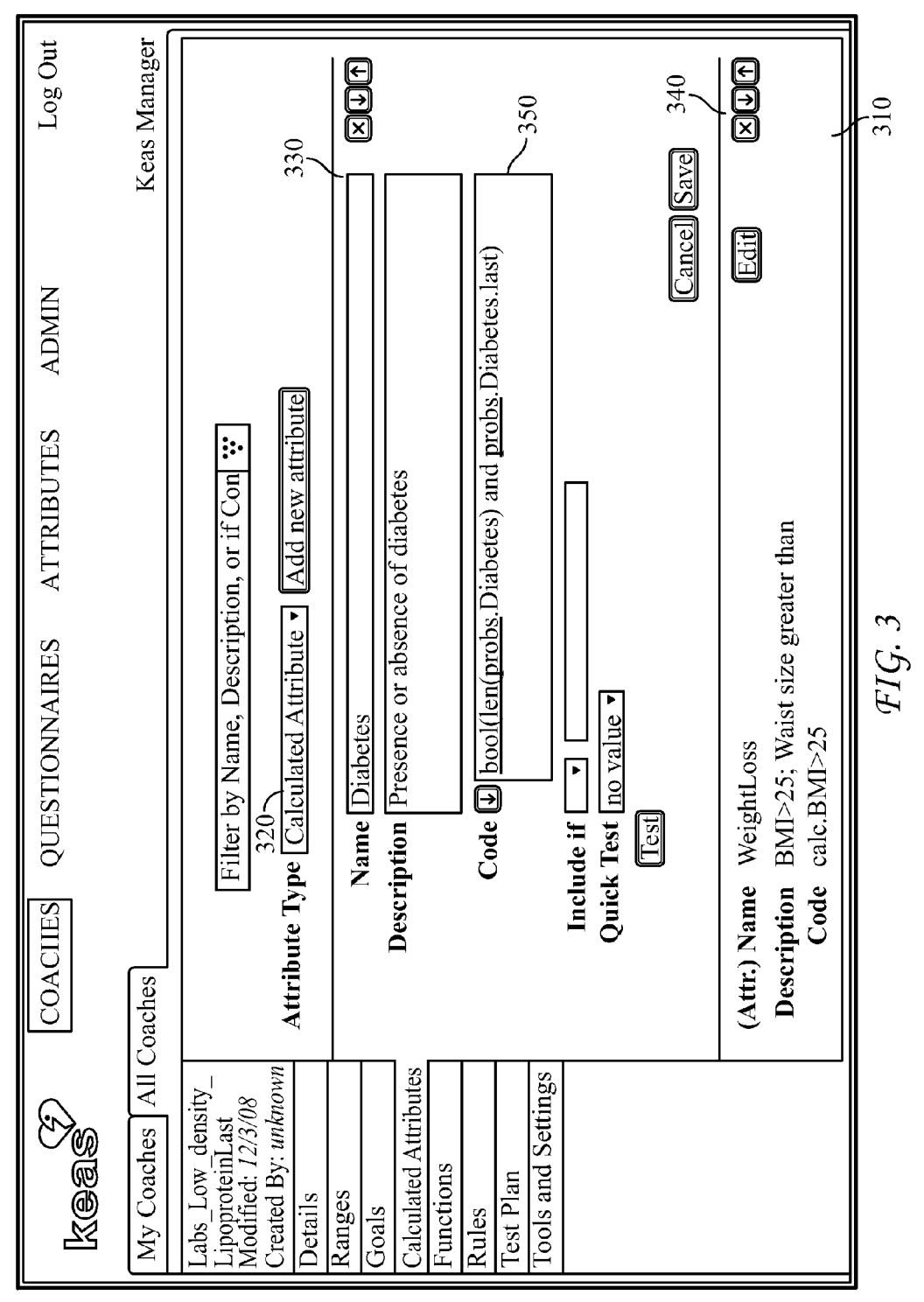
Figure 5:
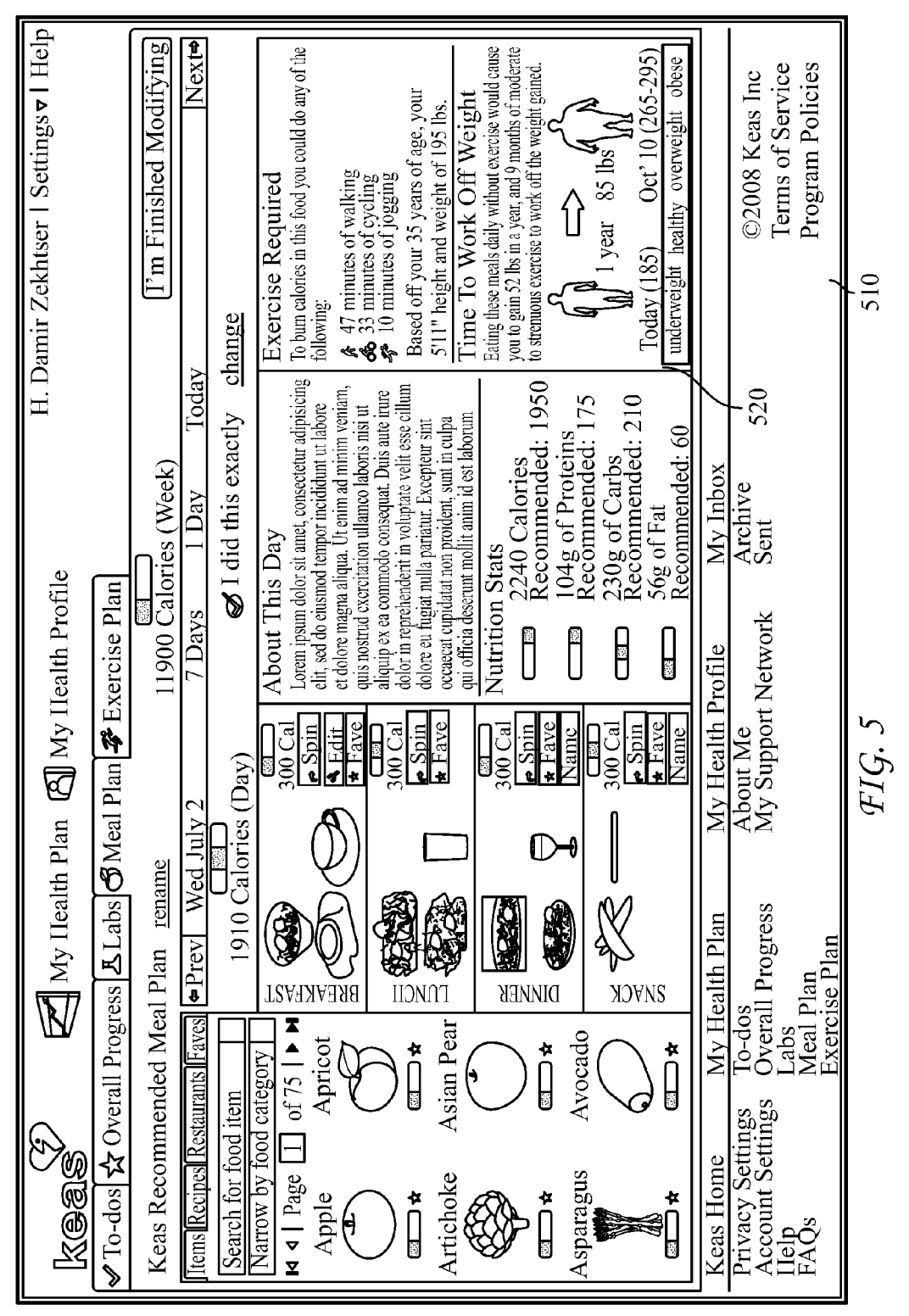
Figure 6:
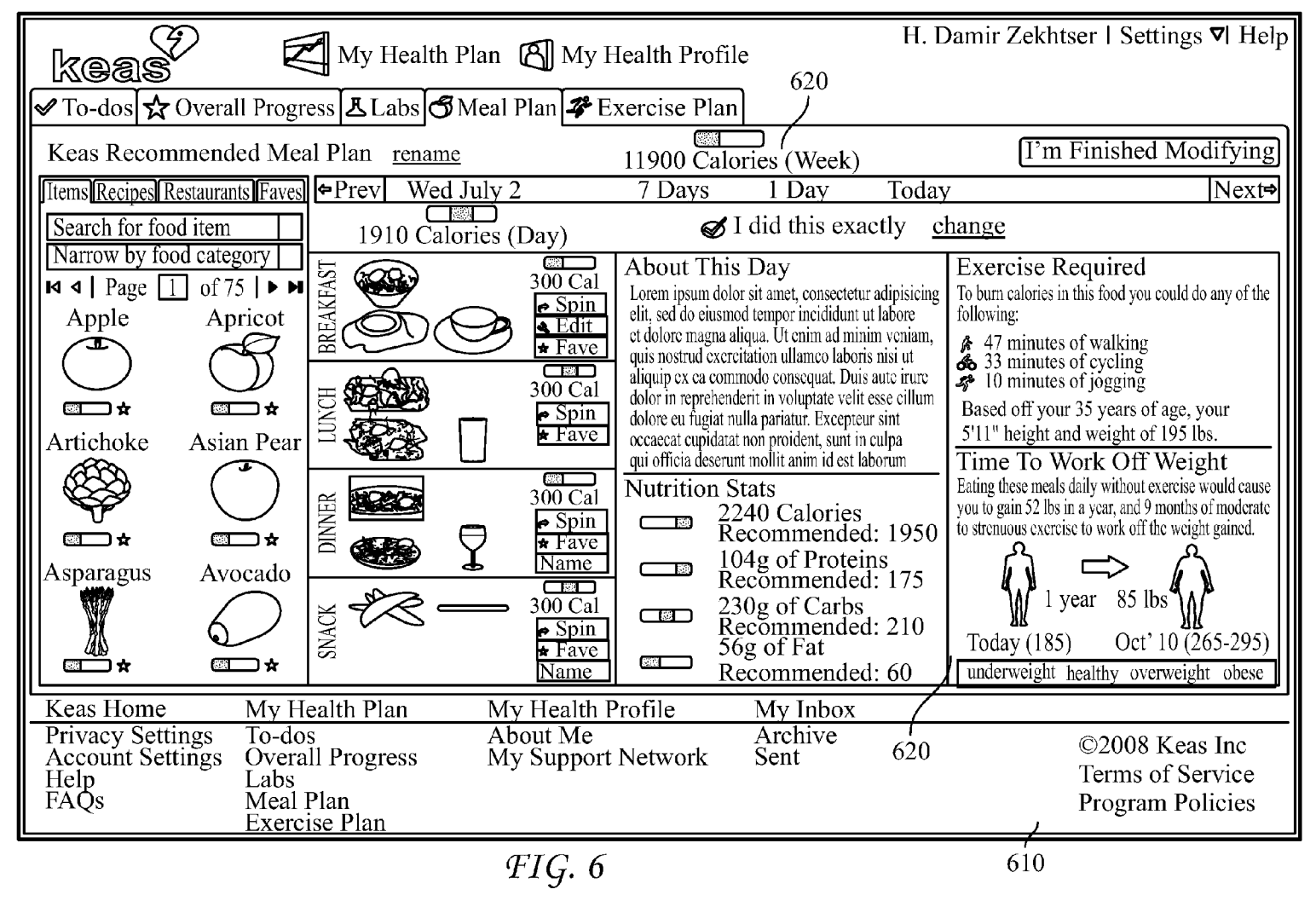

Application server 120 may be implemented in a general computing device that otherwise communicates with data store 110 and network server 130. An example of such a device is the general computing system illustrated in FIG. 7. Application server 120 as illustrated in FIG. 1 includes protocol authoring application 122 and coaching engine 124. Protocol authoring application 122 may by executed by a processor to provide interface data concerning a graphical interface to a client device (e.g., client 150). This interface data may then be executed and rendered as an interface by a client 150 application such as a web browser or Java Virtual Machine. The interface generated from the interface data can be used by author 155 at client 150 for authoring a protocol related to health coaching. The protocol authoring interface as generated from execution of the protocol authoring application 122 can include HTML, XML, scripts, or other code for rendering an authoring interface at client 150. Exemplary interfaces for authoring a protocol are illustrated in FIGS. 3-4 as discussed in greater detail herein. Exemplary interfaces generated from interface data are illustrated in FIGS. 5-6.

Coaching engine 124 is executable by a processor (not shown) at application server 120 to administer a user health coach protocol, where the administration includes generation and management of user attributes, goals, ranges, and rules. Attributes, goals, ranges and rules can be configured in response to input data received from an author 155 at client 150. Coaching engine 124 may be implemented as or may invoke a risk factor engine 126, which executes on user health data to identify user health risks and perform actions based on the user health data. The risk factor engine 126 may be its own independent engine or integrated as a functional part of coaching engine 124. The risk factor engine 126 may communicate with other network services over network 140 to obtain data used to determine risk.

Protocol authoring engine 122 is executed at the application server 120 to access, process, and transmit interface data to client 150 via network server 130 and network 140. The client 150 receives the interface data over network 140 and renders an interface from the interface data in a browser application or other client application, which provides the interface to an author 155. The client 150 may then receive input from an author 155 and transmit input data based on the input to coaching engine 124 and/or risk factor engine 126 on application server 120 or data store 110 over network 140 and network server 130. The input data can include the received input, or data identifying the input, as well as routing information for data packets intended for coaching engine 124 and/or risk factor engine 126. Details of setting attributes, goals, ranges and rules are discussed in more detail below with respect to FIG. 2.

Coaching engine 124, which may include the functionality of risk factor engine 126, may access user health data from data store 110 and process the user health data to perform actions. Coaching engine 124 may incorporate other user profiles to determine user health risk, for example by comparing the user health data to health data of other users. The user health data may include user attributes, goals, ranges, rules, and other data associated with the health of a user. The user health data may be retrieved and used to populate one or more interfaces 122. Moreover, data received as input by a client 150 may be transmitted to coaching engine 124 and/or risk factor engine 126 and stored in data store 110.

Coaching engine 124 can process the goals, attributes and rules to provide alerts, suggestions, updated goals, status and calculated attributes, and other content for a user 165. For example, coaching engine 124 can include or invoke the aforementioned risk factor coaching engine 126, which receives user health data indicating user food consumption trend and adjusts a predicted life span value and weight prediction value for the user based on the user food consumption data. The content can be provided to a user through a coaching interface provided through client 160.

User 165 at client 160 may perform a login with a service provided by coaching engine 124 and receive interface data as a browser application content page. The interface data may include any updates for the user health status, including updated user goals, attribute values, and results of executed rule expressions. The interface data may additionally include information generated through the execution of the risk factor engine 126 such as predicted weight data for the user based on current user consumption trends, such as the predicted weight data shown in FIG. 5.

Network 140 is inclusive of any communication network such as the Internet, Wide Area Network (WAN), Local Area Network (LAN), intranet, extranet, private network, or other network. Application server 120 may be accessed via network server 130. Network server 130 can receive and process requests from clients 150-160. Processing the requests may include sending a request to coaching engine 124 on application server 120, receiving a response from coaching engine 124, or forwarding that response to a requesting client.

Figure 7:
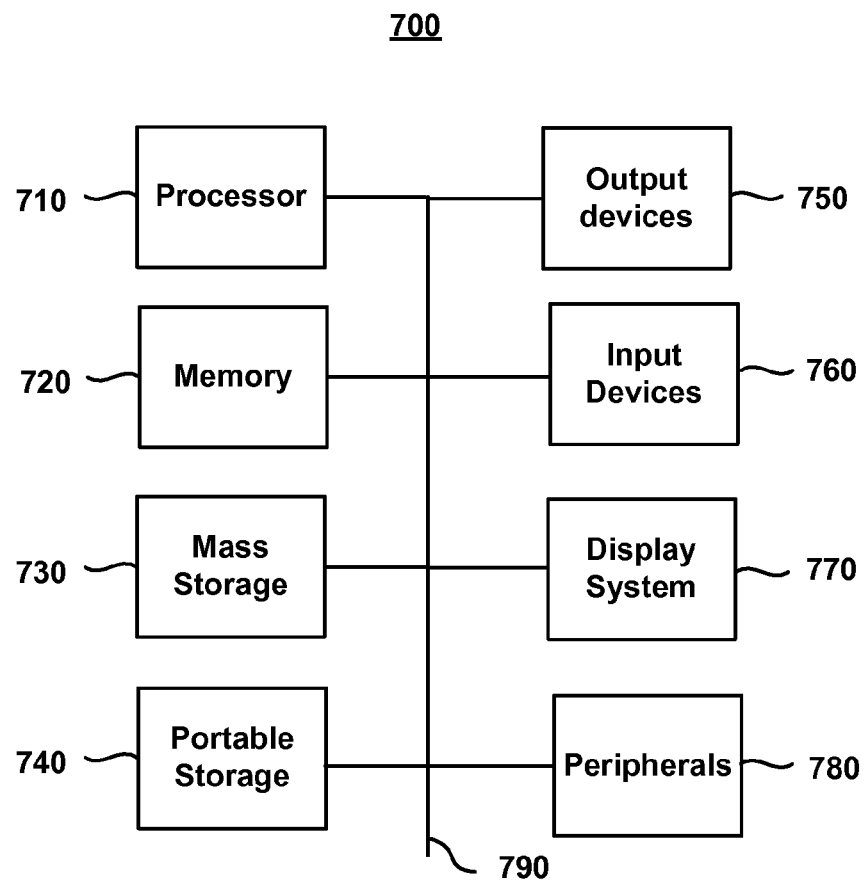
FIG. 7 illustrates a computing system that may be used to implement an embodiment of the present invention

Clients 150 and 160 are inclusive of a general purpose computing device capable of accessing information over a network like that illustrated in FIG. 7. Client 150, specifically, can generate the input data based on input received from author 155. Input data may be received at the client 150 through an interface generated from interface data received from execution of the protocol authoring application 122 over network 140.

Clients 150 and 160 may be implemented as computing devices such as workstations, servers, lap top computers, mobile devices, or other computing devices that can communicate over network 140. Client 150 may include a browser application for rendering coach protocol authoring interface data as a web page interface. Client 160 may include a browser application for rendering coach interface data as web pages interfaces for accessing user health updates and content. Clients 150 and 160 may also use other interfaces to access and communicate with application server 120, such as short message service (SMS), multimedia message service (MMS), the protocol used by "Twitter" of Twitter, Inc., and other protocols.

Figure 2:
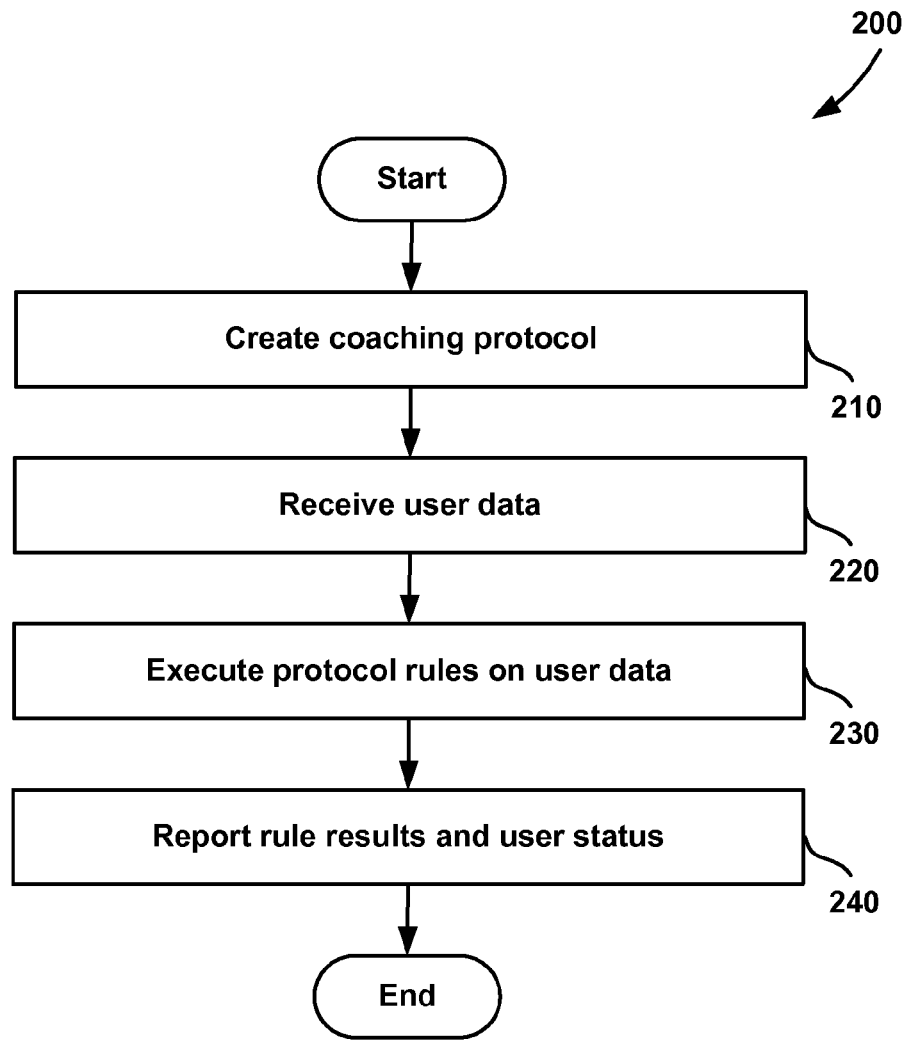
FIG. 2 illustrates a method for providing automated coaching.

FIG. 2 illustrates a method 200 for providing automated coaching. Coaching engine 124 and its corresponding risk factor engine 126 functionality can be implemented as software stored in memory on application server 120 and executed by a processor to perform the method of FIG. 2. As illustrated on FIG. 2, a coaching protocol is created at step 210. The protocol can be generated based on author input received through one or more interfaces derived or rendered from protocol authoring interfaces rendered at client 150. Protocol authoring application 122 transmits interface data to be rendered as an interface at client 150. An author 155 provides input to client 150 through the rendered interface and the client 150 transmits input data to coaching engine 124 via network 140 and network server 130.

Creating a coaching protocol can include setting user ranges, attributes, goals and rules authored by a protocol author 155. A coaching protocol can be created as a new protocol or inherit at least a portion of one or more pre-existing coaching protocols. Ranges can be set by a protocol author for one or more user attribute values with one or more ranges for each attribute. User attributes can include simple attributes and calculated attributes. Simple attributes can be provided by a user or some other source and stored as they are received. Calculated attributes can be derived from the simple attributes, other calculated attributes, and/or other data. For example, a simple attribute may be user weight, and a calculated attribute may a user's body mass index (BMI) calculated as the user weight in pounds multiplied by a constant and divided by the square of the user height in inches. A range may be created for the calculated BML indicating that a BMI value over 30 is labeled as "obese."

A trend function is an operation that evaluates the trend of an attribute value over time. A trend function can determine if a particular attribute value has increased over time, has surpassed a particular value a certain number of times over a time period, whether the attribute value experienced a particular rate of increase decrease over time, or some other attribute trend. For example, a trend function may determine if a weight attribute for a user experiences abnormal fluctuation over a period of time.

A user goal can be set for any number of user attributes. The goal can specify an attribute, time, description, timeline and/or other data relating to the goal. Goal input received from a protocol author 155 can be transmitted by client 150 to protocol authoring application 122 or coaching engine 124 I risk factor engine 126, which can store the goal data locally or remotely to data store 110. For example, if a user is determined to be obese according to a BMI value for the user, a goal may automatically be generated for the user to lose ten percent of their body weight over three months.

A user rule can include an expression for evaluation, an action to be taken based on the outcome of the evaluation, and timing or periodicity data indicating when the rule should be evaluated. Evaluation of a rule can result in an action to take with respect to one or more users. An author can configure a rule action as a notification, instructions to exercise, diet, take a lab test, see a particular health care provider, enroll in a program, fill out a questionnaire, improve a value, or some other action. An action may be configured with a degree of urgency or importance. The level of urgency or importance can be communicated to the user as part of performing the action. Rule periodicity information indicates how often a rule action should be performed. An example of a method for creating a coaching protocol is discussed in U.S. patent application Ser. No. 12/360,731, filed Jan. 27, 2009, and entitled "Protocol Authoring for a Health Coaching Service," the content of which is incorporated herein by reference.

After creating the coaching protocol in FIG. 2, user data can be received at step 220. The received data can include user demographic information, attribute values, past medical history, family history, vaccinations, social history, procedures, allergies, lab data, and other data. The user data can be received through user questionnaires provided by the health coach service, data provided from medical facilities, lab test results, user input provided through client 160, or other sources.

Protocol rules can be executed with respect to the user data according to the coaching protocol at step 230 and as shown in FIG. 3. The protocol rules are executed by coaching engine 124 according to the authored protocol. Protocol rules can be executed through execution of one or more coaches periodically, based on a previous action, or in response to some other event such as a user data change. Coaches can be executed for a user at least once a day.

Executing protocol rules includes retrieving a health service user list by coaching engine 124. The health service user list can be stored on application server 120 or data store 110 and includes a list of users participating in the health service. Coach engine 124 can then retrieve a coach list for each user in the user list. The coach list can be retrieved from application server 120 or data store 110 and includes a list of coaches (e.g., executable coach objects) to execute for each particular user. Each coach list may include an executable root coach for the user and may contain one or more additional executable coaches. As the root coach is executed, the root coach may enroll the user in additional coaches (e.g., the root coach software may add additional coach objects to the user's coach list) such as a risk factor coach as implemented through risk factor engine 126. A user may also choose to be enrolled in a coach.

The one or more coaches listed in a user coach list are selected by coaching engine 214 to be executed by a processor. Coaching engine 124 can first execute a root coach for a user, followed by execution of additional coaches in the order the coaches were added to the user coach list.

Each coach instance, or coach, can retrieve rules and actions. The rules can include an expression with one or more attributes and be retrieved by a coach instance from application server 120 or from data store 110. Actions can also be retrieved from application server 120 or data store 110. The retrieved rules are then executed by the coach instance to determine if an action should be performed based on an attribute value or a trend. A trend function is a type of expression that evaluates the trend of an attribute value over time. For example, a rule may perform an action of enlisting a user in a diet program if a user's body mass index has increased greater than a threshold rate over a period of time.

Once a coach instance is created and the coach rule is evaluated, a determination is made as to whether the expression is evaluated to be true. If a rule expression for a coach is evaluated to be true, the coach instance containing the expression determines the last time the action corresponding to the expression was performed. Coaching engine 124 may query a user action log on application server 120 or data store 110 for the most recent entry for the particular action.

For expressions evaluated to be true, the date the corresponding action was last performed is compared to a periodicity period for the expression by the coaching instance. If the time period between the last performance of the action and the current time is less than the periodicity period, the action is not performed. If the time period since the last time the action was performed is greater than the periodicity period, the action corresponding to the evaluated expression can be performed by the coach instance. An example of a method for executing a protocol by a coaching engine is discussed in U.S. patent application Ser. No. 12/434,574, filed May 1, 2009 and entitled "Coaching Engine for a Health Coaching Service," the content of which is incorporated herein by reference.

A risk factor coaching engine 126 may execute protocol rules on user data related to user health risks. The health risk user data may include attributes for a user condition, habit, family history, or statistic that may negatively affect or cause risk to the health of a user. For example, a risk factor coaching engine 126 may be executed to evaluate a rule which identifies the risk of heart disease. Heart disease risks may be identified using health risk attributes such as user age, family history of heart disease, smoking habits, cholesterol, blood pressure, BMI, diabetes, stress, and alcohol consumption.

The risk factor coaching engine 126 may apply a rule to each health risk attribute to determine if the attribute value may contribute to a health risk and a corresponding action should be triggered. For example, if a user smokes and has high blood pressure, an action may be performed to provide the user with information on how to stop smoking and set up an appointment between the user and a health provider for an examination and possible high blood pressure medication. An action may include setting a goal for the user, such as to set a goal of engaging in at least 30 minutes of exercise for four days a week, thereby contributing to losing weight and reducing blood pressure.

The risk factor coaching engine 126 may also calculate a user health score based on user health data. The user health score can be associated with an expected life span for the user or an "effective" age for the user which reflects the health of the user. The user health score can also be associated with a predicted value, such as a predicted weight for the user. An expected life span can be determined based on the value of certain attributes related to risk factors, and the effect of the values on the lifespan of the user. For example, a study by the University of California and published in the April 2000 Berkeley Wellness Letter has shown that the life span of a user may be reduced by 11 minutes for each cigarette smoked, or by about two months for each year a user smoked a pack of cigarettes per day. Using the trends found in this study for a user that smoked a pack of cigarettes a day for ten years, a risk factor coaching engine 126 might predict a user life span for the user as twenty months less than the normal life span. Other trend studies and sources of data can be used to determine the effect of a user health data attribute values on a user health score.

Returning to the method of FIG. 2, after executing protocol rules for a coach instance, one or more actions may be performed and the action results and user status are reported at step 240. The results and status can be reported as an alert, via e-mail, posting within a content page interface provided by the health coach service, or in some other manner.

The action for an expression evaluated to be true is performed or "fired" if the time period has expired since the last time the action was performed. The action can include enrolling the user in a coach or program, such as a diet program or workout program. A rule action may also include providing a user notification, generating a life span prediction, or providing instructions to get a lab test performed, to see a particular health care provider, to fill out a questionnaire, to improve a value, or to take some other action. A user notification may be provided when a user has failed to perform a particular action, when an attribute value has exceeded a threshold, or some other event has been detected. A rule action can be tagged with content such as a blog, pod cast, video, audio, image, or some other data. When the rule is executed, the content can be forwarded to the user as part of the performed action if the conditions for the rule have been met. For a questionnaire, the coach instance may invoke a questionnaire engine to provide the questionnaire to the user. The questionnaire engine may retrieve questions from a questionnaire library, construct the questionnaire, and provide the questionnaire to the user, such as through a coach service web page.

An example of an interface 310 that allows an author 150 to create a calculated attribute for a risk factor is illustrated in FIG. 3. A list of categories for generating a protocol is displayed in left side of the interface, of which "calculated attributes" is currently selected. An attribute type of "calculated attributes" is selected in attribute type box 320. As a result, a list of calculated attributes is listed within the interface, including data for a first calculated attribute 330 and a second calculated attribute 340. Data for the second calculated attribute 340 "WeightLoss" includes summary information for the attribute as well as an icon for selecting to "edit" the calculate attribute. Information for the first calculated attribute 330 "Diabetes" includes detailed information provided as a result of an "edit" button for the first calculated attribute being selected.

The first calculated attribute 330 in interface 310 has a name "Diabetes," a description of "Presence or absence of diabetes," and an expression box 350. The expression box 350 contains the expression which is evaluated to determine the calculated attribute value. The expression is built using lists of attributes and operations available to the coaching engine. For example, the lists may be populated from libraries of attributes and operations stored in data store 110. The expression in expression box 350 is "bool(len(probs.Diabetes) and probs.Diabetes.last)." The expression indicates that the calculated attribute "Diabetes" has a Boolean value derived from the length of the object "probs.Diabetes" and the object "probs.Diabetes.last." The calculated attribute "Diabetes" can be incorporated into a rule that executes an action. The action may recommend diabetes testing if diabetes is not present or diabetes education if diabetes is present.

An example of an interface 410 that allows an author 150 to create a rule for executing on risk factor data is illustrated in FIG. 4. The interface includes input boxes for an author to provide a rule name, description, expression, action, periodicity and other data. The rule name is provided as "LDLHealthyGreaterThan190," the rule description is entered as "Healthy, Non-smoker, LDL>190," and the rule expression is entered as "not calc.HeartDisease and not PreventHeartDisease and not calc.Diabetes and value.LDL>=190." In the expression, the "HeartDisease," "PreventHeartDisease," and "Diabetes" terms identify attributes, the "calc" term indicates that values of the appropriate attribute should be calculated, the "not" term indicates that the value should not have a value of "TRUE," and the "value" and ">=190" indicate that the value of the appropriate attribute should have a value greater than or equal to 190.

The selected rule action is performed if the rule is expression is evaluated to be true. The rule may be comprised of an action and, in some instances, content to provide with an action. The content may be identified by a "tag" associated with the content. In the rule configured in the interface 410, if the "HeartDisease," "PreventHeartDisease," and "Diabetes" attributes are true and the "LDL" attribute has a value greater than or equal to 190, the rule will notify the user with content associated the tag "LDLHealthyGreaterThan190."

FIG. 5 illustrates an interface 510 for providing a user health prediction to a user. The interface 510 illustrates information for a meal plan created for a user, exercise required to burn off the calories in the meal plan, and a prediction of weight gain if no exercise is performed. Weight information window 520 indicates that for the meal and corresponding calories selected by a user through interface 510, a coaching engine predicts the user would gain about eighty-five pounds in one year if the selected food was consumed for a year without exercise. Window 520 provides information indicating that the user's predicted weight could range between 265 and 295 pounds and that the user would be obese as indicated by the large red human figure.

FIG. 6 illustrates an alternative implementation of an interface 610 for providing user health predictions to a user. A prediction of an attribute such as weight or life span for a user can be changed if the user changes parameter data used to generate the prediction. The interface 610 illustrates similar information for a meal plan, exercise required to burn off meal plan calories, and a weight gain prediction as indicated in interface 510 of FIG. 5, but an assumption is made that the user has selected a meal with fewer calories than the meal selected in interface 510. Information window 620 indicates that for the meal and corresponding calories selected by a user through interface 610, a coaching engine predicts the user would gain about fifty-two pounds in one year if the selected food was consumed for a year without exercise. Window 620 also provides information indicating that the user's predicted weight could range between 240 and 260 pounds and that the user would be overweight (rather than obese) as indicated by the yellow human figure.

As illustrated in the interfaces 510 and 610, a user may change the value of one or more attributes to see changes in a prediction of user health. The changed parameter in interfaces 510 and 610 was calorie intake. A prediction of lifespan could be changed based on user input of smoking habits, drinking habits, and other attributes that affect life span. The attribute changes may be received by the interface through a slider bar, text box, clicking of a button, or some other input mechanism. Different predictions may also be calculated for a user based on attribute values and provide in graphical or table format.

FIG. 7 illustrates an exemplary computing system 700 that may be used to implement an embodiment of the present invention. System 700 of FIG. 7 may be implemented in the contexts of the likes of data store 110, application server 120, network server 130, database 122, and clients 150-160. The computing system 700 of FIG. 7 includes one or more processors 710 and memory 710. Main memory 710 stores, in part, instructions and data for execution by processor 710. Main memory 710 can store the executable code when in operation. The system 700 of FIG. 7 further includes a mass storage device 730, portable storage medium drive(s) 740, output devices 750, user input devices 760, a graphics display 770, and peripheral devices 780.

The components shown in FIG. 7 are depicted as being connected via a single bus 790. However, the components may be connected through one or more data transport means. For example, processor unit 710 and main memory 710 may be connected via a local microprocessor bus, and the mass storage device 730, peripheral device(s) 780, portable storage device 740, and display system 770 may be connected via one or more input/output (I/O) buses.

Mass storage device 730, which may be implemented with a magnetic disk drive or an optical disk drive, is a non-volatile storage device for storing data and instructions for use by processor unit 710. Mass storage device 730 can store the system software for implementing embodiments of the present invention for purposes of loading that software into main memory 710.

Portable storage device 740 operates in conjunction with a portable non-volatile storage medium, such as a floppy disk, compact disk (CD) or digital video disc (DVD), to input and output data and code to and from the computer system 700 of FIG. 7. The system software for implementing embodiments of the present invention may be stored on such a portable medium and input to the computer system 700 via the portable storage device 740.

Input devices 760 provide a portion of a user interface. Input devices 760 may include an alpha-numeric keypad, such as a keyboard, for inputting alpha-numeric and other information, or a pointing device, such as a mouse, a trackball, stylus, or cursor direction keys. Additionally, the system 700 as shown in FIG. 7 includes output devices 750. Examples of suitable output devices include speakers, printers, network interfaces, and monitors.

Display system 770 may include a liquid crystal display (LCD) or other suitable display device. Display system 770 receives textual and graphical information, and processes the information for output to the display device.

Peripherals 780 may include any type of computer support device to add additional functionality to the computer system. For example, peripheral device(s) 780 may include a modem or a router.

The components contained in the computer system 700 of FIG. 7 are those typically found in computer systems that may be suitable for use with embodiments of the present invention and are intended to represent a broad category of such computer components that are well known in the art. Thus, the computer system 700 of FIG. 7 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Palm OS, and other suitable operating systems.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims appended hereto.

What is claimed is:

1. A method for processing risk factors for a user, comprising:

receiving protocol data for creating a risk factor engine by an application stored and executed at a computing device, the risk factor engine stored in memory and executable by a processor to process a first set of stored user health data for a user, wherein the protocol data includes a rule and one or more health attribute values, the rule and the one or more health attribute values each including a computer programming expression editable by an administrator; and determining a user health score through execution of the risk factor engine by the processor and based on the user health data, wherein determining the user health score includes evaluating the expressions of the one or more health attribute values by inputting the user health data to calculate one or more calculated health attribute values, and then evaluating the expression of the rule by inputting the one or more calculated health attribute values to calculate the user health score.

2. The method of claim 1, further comprising determining a predicted user weight based on the one or more calculated health attribute values.

3. The method of claim 1, wherein the health data includes a food consumption trend generated from food consumption data received from the user.

4. The method of claim 3, further comprising determining a predicted user weight based on the food consumption trend.

5. The method of claim 4, further comprising displaying the predicted user weight through a graphical interface as an image of a human figure, the size and the shape of the human figure determined by the value of the predicted user weight.

6. The method of claim 1, wherein the expression of the rule returns a predicted user life span based on the one or more calculated health attribute values.

7. The method claim 6, further comprising displaying the predicted user life span through a graphical interface.

8. The method of claim 1, further comprising determining a predicted user attribute based on a trend calculated from a portion of the user health data.

9. The method of claim 6, wherein the user health score is associated with the predicted user life span.

10. A non-transitory computer readable storage medium having embodied thereon a program, the program being executable by a processor to perform a method for processing risk factors for a user, the method comprising:
   receiving protocol data for creating a risk factor engine by an application stored and executed at a computing device, the risk factor engine stored in memory and executable by a processor to process a first set of stored user health data for a user, wherein the protocol data includes a rule and one or more health attribute values, the rule and the one or more health attribute values each including a computer programming expression editable by an administrator; and
   determining a user health score through execution of the risk factor engine by the processor and based on the user health data, wherein determining the user health score includes evaluating the expressions of the one or more health attribute values by inputting the user health data to calculate one or more calculated health attribute values, and then evaluating the expression of the rule by inputting the one or more calculated health attribute values to calculate the user health score.

11. The non-transitory computer readable storage medium of claim 10, wherein the method further comprises determining a predicted user weight based on the one or more calculated health attribute values.

12. The non-transitory computer readable storage medium of claim 10, wherein the health data includes a food consumption trend generated from food consumption data received from the user.

13. The non-transitory computer readable storage medium of claim 12, wherein the method further comprises determining a predicted user weight based on the food consumption trend.

14. The non-transitory computer readable storage medium of claim 13, wherein the method further comprises displaying the predicted user weight through a graphical interface as an image of a human figure, the size and the shape of the human figure determined by the value of the predicted user weight.

15. The non-transitory computer readable storage medium of claim 10, wherein the expression of the rule returns a predicted user life span based on the one or more calculated health attribute values.

16. The non-transitory computer readable storage medium claim 15, wherein the method further comprises displaying the predicted user life span through a graphical interface.

17. The non-transitory computer readable storage medium of claim 10, wherein the method further comprises determining a predicted user attribute based on a trend calculated from a portion of the user health data.

18. The non-transitory computer readable storage medium of claim 15, wherein the user health score is associated with the predicted user life span.

\* \* \* \* \*